United States Patent [19]
Bonne

[11] Patent Number: 5,303,167
[45] Date of Patent: Apr. 12, 1994

[54] ABSOLUTE PRESSURE SENSOR AND METHOD

[75] Inventor: Ulrich Bonne, Hopkins, Minn.

[73] Assignee: Honeywell Inc, Minneapolis, Minn.

[21] Appl. No.: 666,780

[22] Filed: Mar. 8, 1991

[51] Int. Cl.$^5$ .............................................. G01N 9/00
[52] U.S. Cl. .................... 364/556; 73/204.26; 364/558; 374/43
[58] Field of Search .............. 364/556, 557, 558, 571.01–571.08; 73/204.14, 204.15, 204.16, 204.17, 204.24, 204.25, 204.26, 204.33; 374/43, 44, 29, 144, 113, 166

[56] References Cited

U.S. PATENT DOCUMENTS

| | | | |
|---|---|---|---|
| 4,478,076 | 10/1984 | Bohrer | 73/204.26 |
| 4,501,144 | 2/1985 | Higashi et al. | 73/204.26 |
| 4,624,137 | 11/1986 | Johnson et al. | 73/204.26 |
| 4,682,503 | 7/1987 | Higashi | 73/204 |
| 4,739,657 | 4/1988 | Higashi et al. | 73/204.18 |
| 4,765,188 | 8/1988 | Krechmery et al. | 364/558 X |
| 4,783,996 | 11/1988 | Ohta et al. | 73/204.26 X |
| 4,825,693 | 5/1989 | Bohrer et al. | 73/204.25 |
| 4,835,717 | 5/1989 | Michel et al. | 364/556 X |
| 4,944,035 | 7/1990 | Aagardl et al. | 364/556 |
| 4,956,793 | 9/1990 | Bonne et al. | 364/558 |
| 4,958,520 | 9/1990 | Trommler et al. | 364/558 X |
| 5,046,858 | 9/1991 | Tucker | 364/557 X |

Primary Examiner—Kevin J. Teska
Attorney, Agent, or Firm—Michael B. Atlass; Gregory A. Bruns

[57] ABSTRACT

A sensor that provides absolute pressure independent of the composition of the measured gas includes a large microbridge used to determine the thermal conductivity and specific heat of the gas and a small microbridge pressure sensor comprising a heated element suspended over a V-groove. Voltages and currents associated with heated elements of both microbridges are measured and used in an equation to provide an absolute pressure value.

10 Claims, 8 Drawing Sheets

ABSOLUTE PRESSURE SENSOR AND METHOD

BACKGROUND OF THE INVENTION

The present invention relates to the measurement of certain physical properties of gases to support the determination of the absolute pressure of a gas. U.S. Pat. No. 4,682,503 dated Jul. 28, 1987 and assigned to Honeywell Inc. describes the use of a microscopic size thermal conductivity-type absolute pressure sensor fabricated on a silicon chip. The sensor includes an elongated V-groove anistropically etched in the silicon with a heated silicon nitride bridge element extending over the surface of the V-groove. U.S. Pat. No. 4,682,503 describes the response of the pressure sensor to air and is not concerned with the variation in sensed absolute pressure due to the composition of the gas being sensed. Applications for accurate absolute pressure readings require that the response of this sensor be compensated for the composition of the specific gas being used.

A need exists in the field of gas measurements for a method of determining the absolute pressure P of a gas which is independent of the makeup or composition of that gas.

SUMMARY OF THE INVENTION

The present invention overcomes disadvantages associated with other methods of measurement of absolute pressure based on 1) fragile membranes which are prone to break when exposed to over-pressures, 2) Pirani-type gauges which are sensitive to the composition of the gas environment to be measured, 3) mercury manometers which require the use of toxic mercury and do not easily lend themselves to automated or electronic readout, and 4) vibratory sensors which are costly to manufacture and require complex electronics.

The present invention utilizes a single silicon based sensor chip including a large microbridge and a small microbridge. A static sample of the gas of interest is present at both microbridges. The large microbridge includes a heater and a sensor coupled to the gas. The thermal conductivity, temperature and specific heat on a unit volume basis of the gas are determined using the large microbridge. Heater voltage and heater current are measured for both the large and the small microbridges. The absolute pressure of the gas is then determined as a function of the measured values for thermal conductivity, specific heat, temperature, and voltages and currents of the large and small microbridges.

DESCRIPTION OF THE PREFERRED EMBODIMENT

Figure 1:
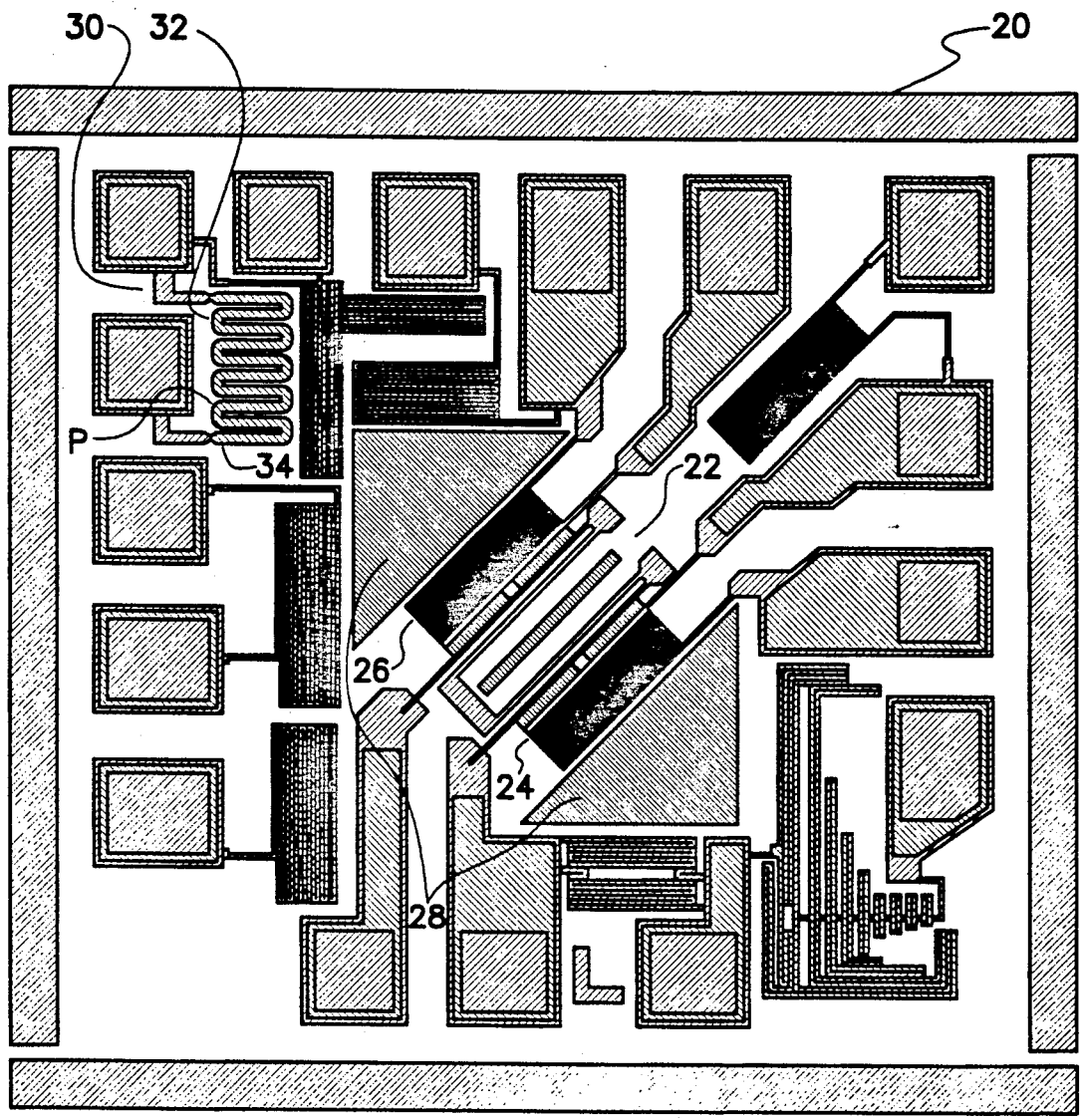
FIG. 1 is a drawing of two microbridge devices incorporated into a single silicon chip.

The present invention is directed to a system which enables the determination of the absolute pressure of a gas independently of the type of gas. The system utilizes a two microbridge sensor structure located within a single silicon chip 20 as shown in FIG. 1 For ease of discussion the microbridge structure will be referred to as a large or first microbridge 22 and a small or second microbridge 30. The small microbridge has a key influence on, but does not by itself completely determine the pressure.

Figure 2:
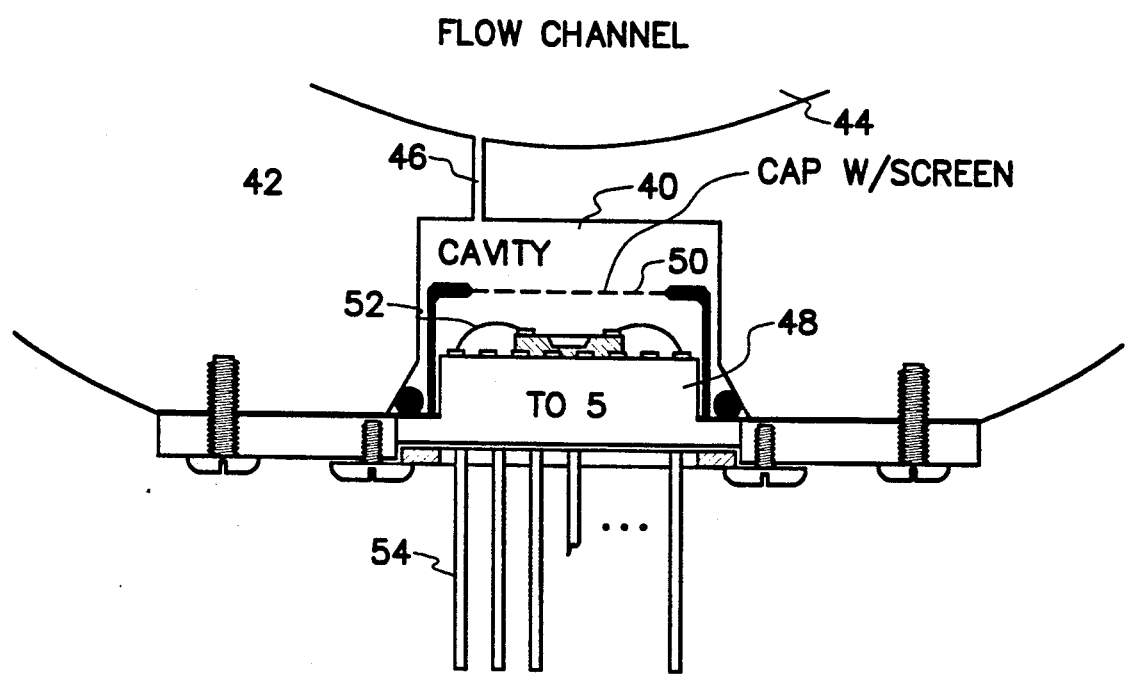
FIG. 2 is a cross sectional view of the packaged chip of FIG. 1 in an arrangement for sensing absolute pressure.

The sensor with which the present invention has been implemented is shown in FIG. 2. Sensor 20 is placed in a dead end cavity 40 and protected from direct exposure to any flow which may occur in the space or pipe 44. Piping or conduit 42 surrounding space 44 has a passage 46 leading to cavity 40. In FIG. 2 silicon sensor 20 is shown in a TO5 package 48 with the cap of the package modified to include a screen 50 to expose sensor 20 to the cavity gas and its pressure. Lead 52 to the chip and leads 54 from the package are also shown.

FIG. 1 illustrates a single silicon sensor chip 20 which includes a large microbridge structure 22 including a heated element 24 a sensor element 26 suspended over a cavity 28. Details of this microbridge structure and particularly its usefulness in determining the thermal conductivity k and specific heat $c_p$ of a gas are set forth in U.S. Pat. No. 4,944,035 which is hereby incorporated by reference.

FIG. 1 also illustrates a small microbridge structure 30 which includes elongated V- groove 34 etched in the silicon with a heated element 32 extending over the surface of the V- groove. Details of this microbridge structure and its operation are set forth in U.S. Pat. No. 4,682,503 which is hereby incorporated by reference.

Figure 6:
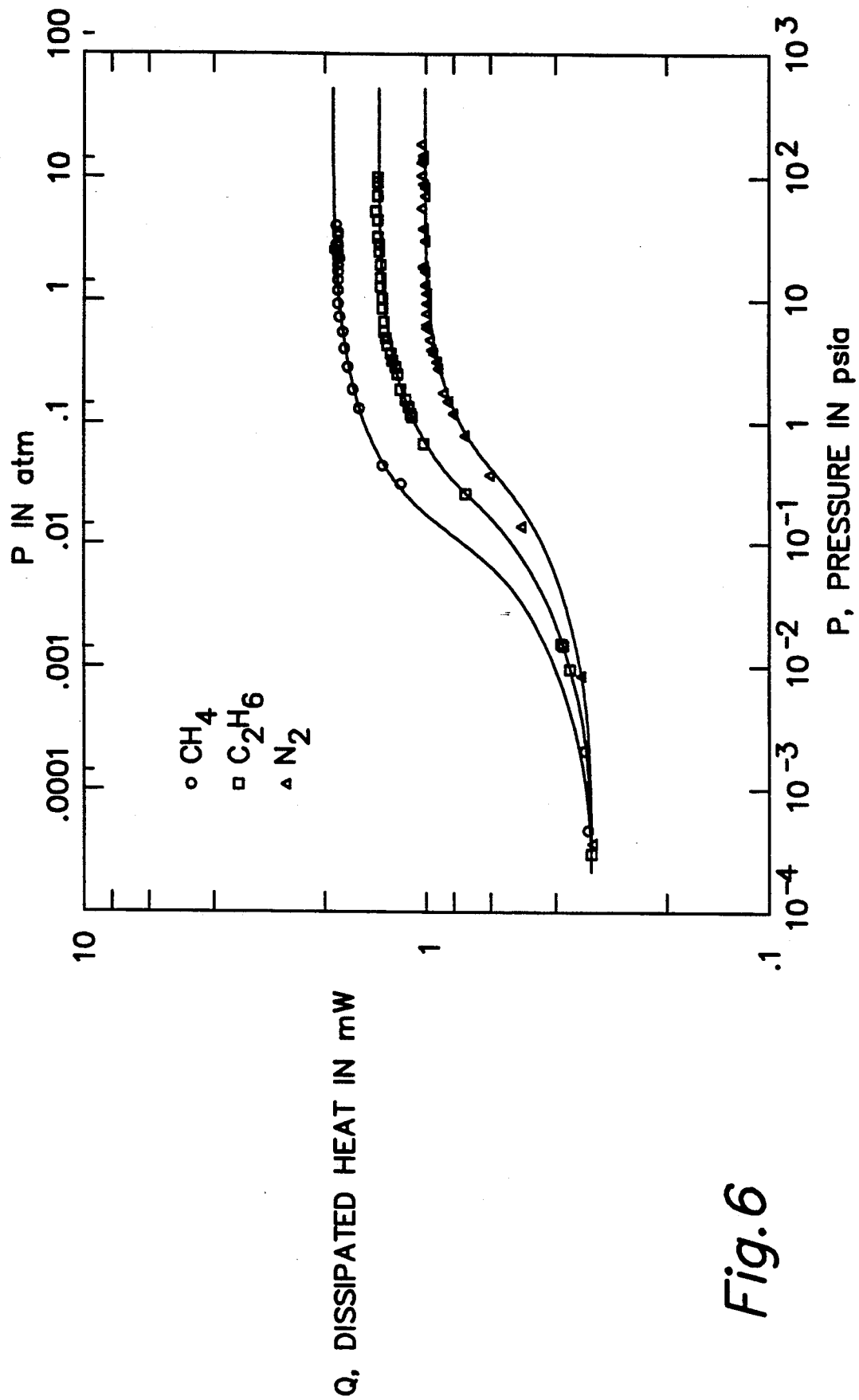
FIG. 6 is a plot of the heat dissipated by a microbridge heater vs gas pressure for $CH_4$, Air and Argon.
Figure 6A:
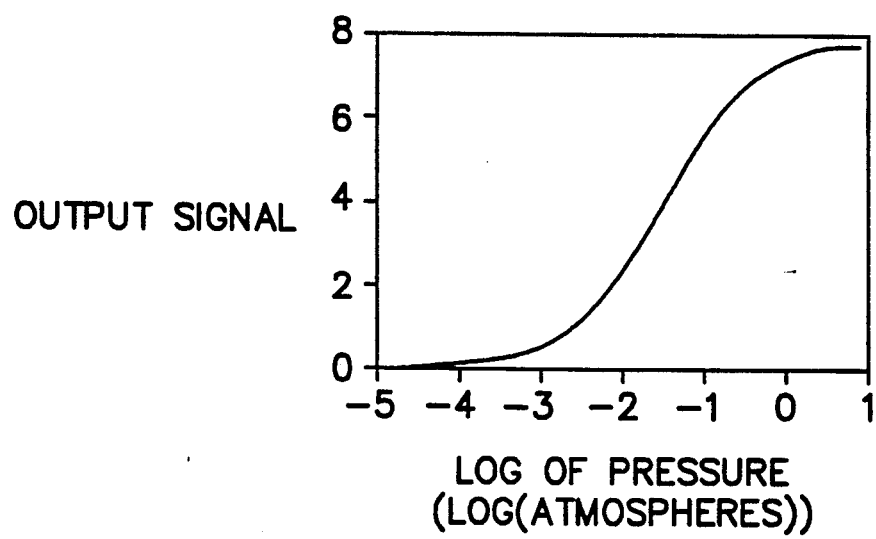
FIG. 6a shows the measured response to air pressure of a small microbridge structure.

FIG. 6a illustrates the characteristic response to air of the small microbridge structure 30 which is of the type described in U.S. Pat. No. 4,682,503.

FIG. 6 illustrates the response of the small microbridge structure to gases other than air. FIG. 6 is a plot of the measured heat (Q) in milliwatts (mW) dissipated by a small microbridge sensor 30 in order to maintain the heated element 32 at a constant temperature difference above the ambient or gas temperature. The temperature of the tested sensor element was approximately 85° C. The plot of heat (Q) is shown as a function of the absolute pressure. Methane, ethane and nitrogen were used for the plot of FIG. 6 to illustrate the difference in response as a function of gas composition. As shown, the lighter gas, methane, required the largest amount of heat. The heat dissipated increased as the pressure (P) increased from left to right until a plateau is reached as seen at the right of FIG. 6. No correction for the type of gas has yet been applied in FIG. 6.

Figure 3:
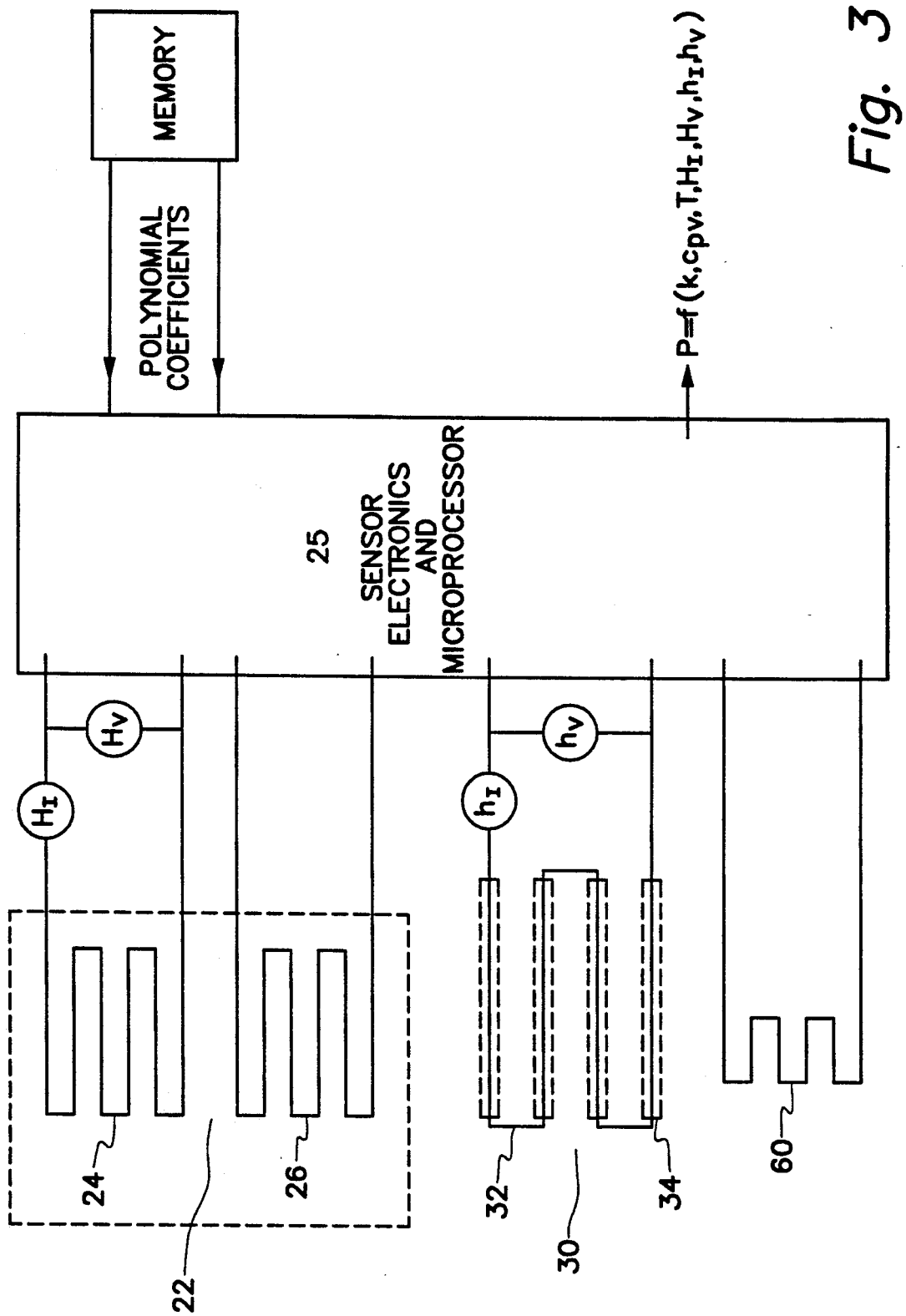
FIG. 3 is a functional diagram of the system of the present invention.

FIG. 3 is a diagram of the present invention. Large microbridge 22 including heated element 24 and sensor 26 are part of silicon sensor chip 20 and are coupled by the gas of interest within cavity 28. Voltage $H_v$ impressed across heated element 24 and current $H_I$ flowing in heated element 24 in order to maintain element 24 at a constant temperature above ambient are controlled and measured by the sensor electronics and microprocessor module 25.

Small microbridge 30 is also part of silicon sensor chip 20. Heated element 32 is suspended over the surface of V- groove 34. Voltage $h_v$ impressed across heated element 32 and current $h_I$ flowing in heated element needed to maintain heated element 32 at a constant temperature above ambient are controlled and measured by the sensor electronics and microprocessor module 25.

Temperature of the gas ($T_g$) is sensed by monitoring one of the available temperature dependent resistors on silicon sensor 20. In FIG. 3 resistor 60 represents a temperature dependent resistor whose resistance is measured and converted to a signal representative of gas temperature ($T_g$) by the sensor electronics and microprocessor module 25.

Module 25 includes sensor signal conditioning electronics, A/D converters, Input/Output ports a clock and other necessary features.

Memory Module 27 provides storage for coefficients needed for determining k, $c_{pv}$, and T in accordance with U.S. Pat. No. 4,944,035. Module 27 also contains coefficients for the polynomial described herein for determining absolute pressure, P.

The accurate determination of absolute pressure with the small microbridge (U.S. Pat. No. 4,682,503) requires that the influence of gas composition be eliminated.

Applicant's invention provides a polynomial that allows the determination of absolute pressure, independent of the type of gas, as a function of the following measured variables:

$$P = f(k, c_{pv}, H_v, H_I, T_g, h_v, h_I) \qquad (1)$$

where: where:
k = thermal conductivity of the gas
$c_{pv}$ = specific heat of the gas in units of energy per (degree and unit volume)
$T_g$ = gas temperature
$H_V$ and $H_I$ = heater voltage and current of the large microbridge and
$h_v$ and $h_i$ = heater voltage and current of the small microbridge The equation for the calculation of absolute pressure (P) is a polynomial of the form:

$$P = \Sigma_i A_i(k^{n1i} c_{pv}^{n2i} T_g^{n3i} H_V^{n4i} H_I^{n5i} h_v^{n6i} h_i^{n7i}) \qquad (2)$$

By the use of well known curve fitting approaches, values for coefficients and exponents may be determined, for example:

$i = 1 \quad A_1 = .0698, n_{11} = \ldots = n_{71} = 0$ $i = 2 \quad A_2 = .018813 \; n_{12} = -2, n_{22} = -1, n_{32} = 2,$
$\qquad n_{42} = .5, n_{52} = .5, n_{62} = 1, n_{72} = 1$ $i = 3 \quad A_3 = \ldots$ Values of n1i through n7i which would serve to generate an accurate representation of P ranged from −3 to +3.

Figure 7:
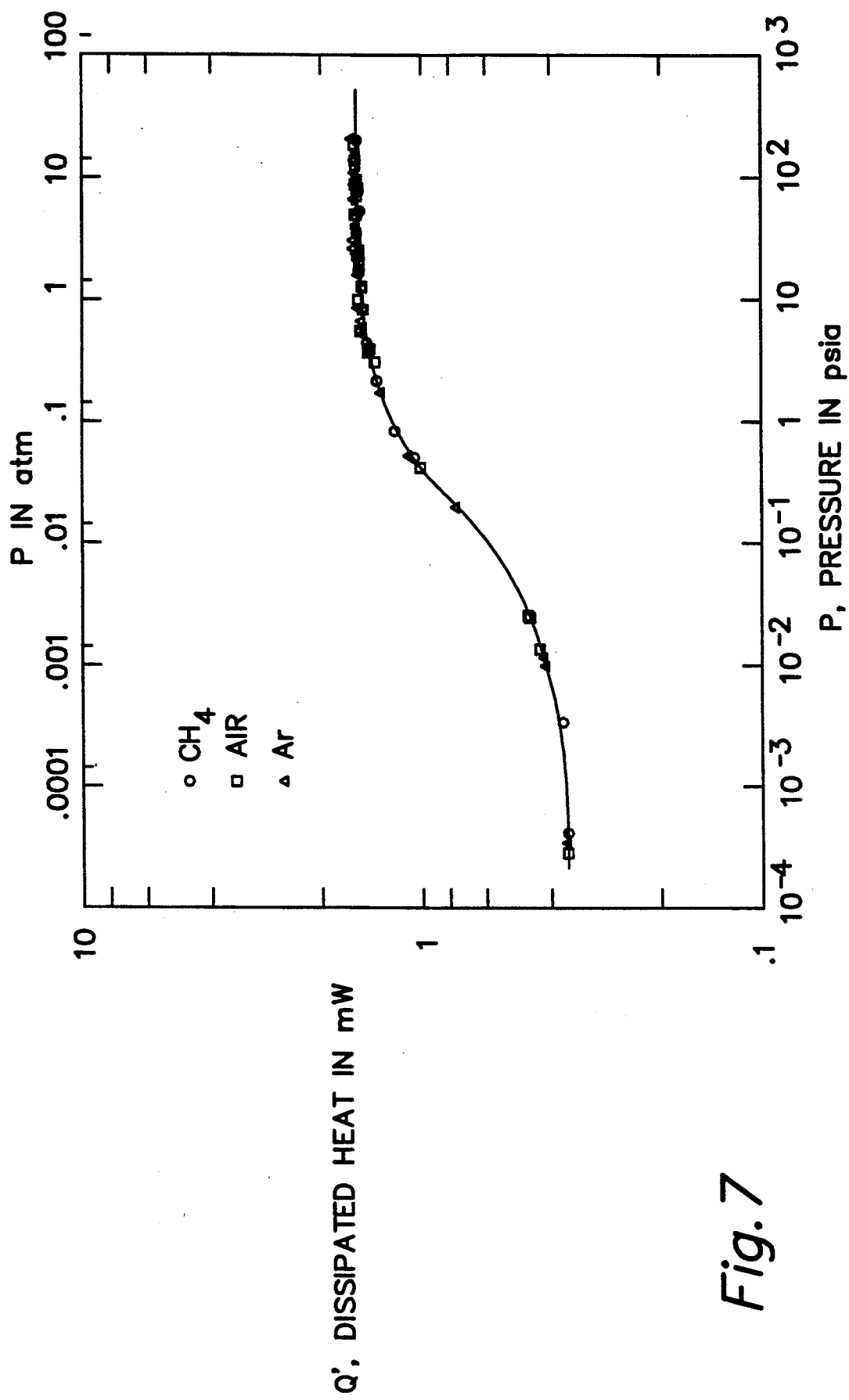
FIG. 7 is a plot of the heat dissipated by a microbridge heater vs pressure for the gases of FIG. 6, after gas composition correction.

FIG. 7 is a plot of a corrected heat dissipated, Q', where Q' is determined by applying a correction to Q after measuring thermal conductivity (k), specific heat ($c_{pv}$) and temperature ($T_g$) of the gas and also measuring the voltage and current for both the large microbridge 22 and the small microbridge 30.

FIG. 7 is a plot of the data of FIG. 6, except a correction for the thermal conductivity and specific heat of the used gases was made to demonstrate that such a correction is feasible, and if applied correctly, the influence of gas composition can be eliminated, and a pure pressure signal obtained.

Figure 4:
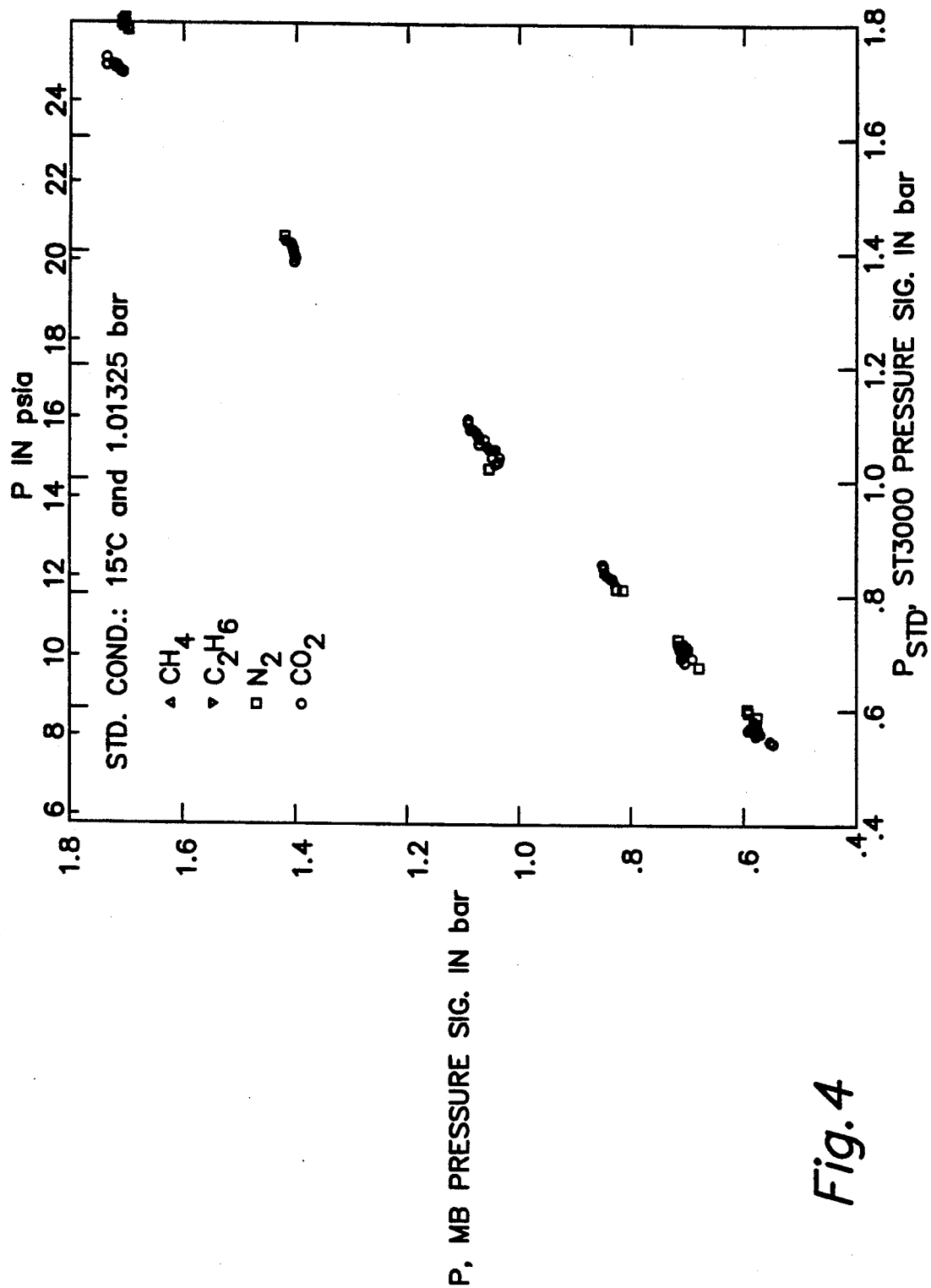
FIG. 4 is a plot of a comparison between a microbridge system of the present invention and a precision ST 3000 pressure sensor.

FIG. 4 is a plot of a comparison between a microbridge system utilizing the present invention and a precision Honeywell ST 3000 pressure sensor, which served as the measurement standard or reference pressure sensor.

FIG. 4 illustrates that applicant's algorithm provides an accurate determination of absolute pressure.

Figure 5:
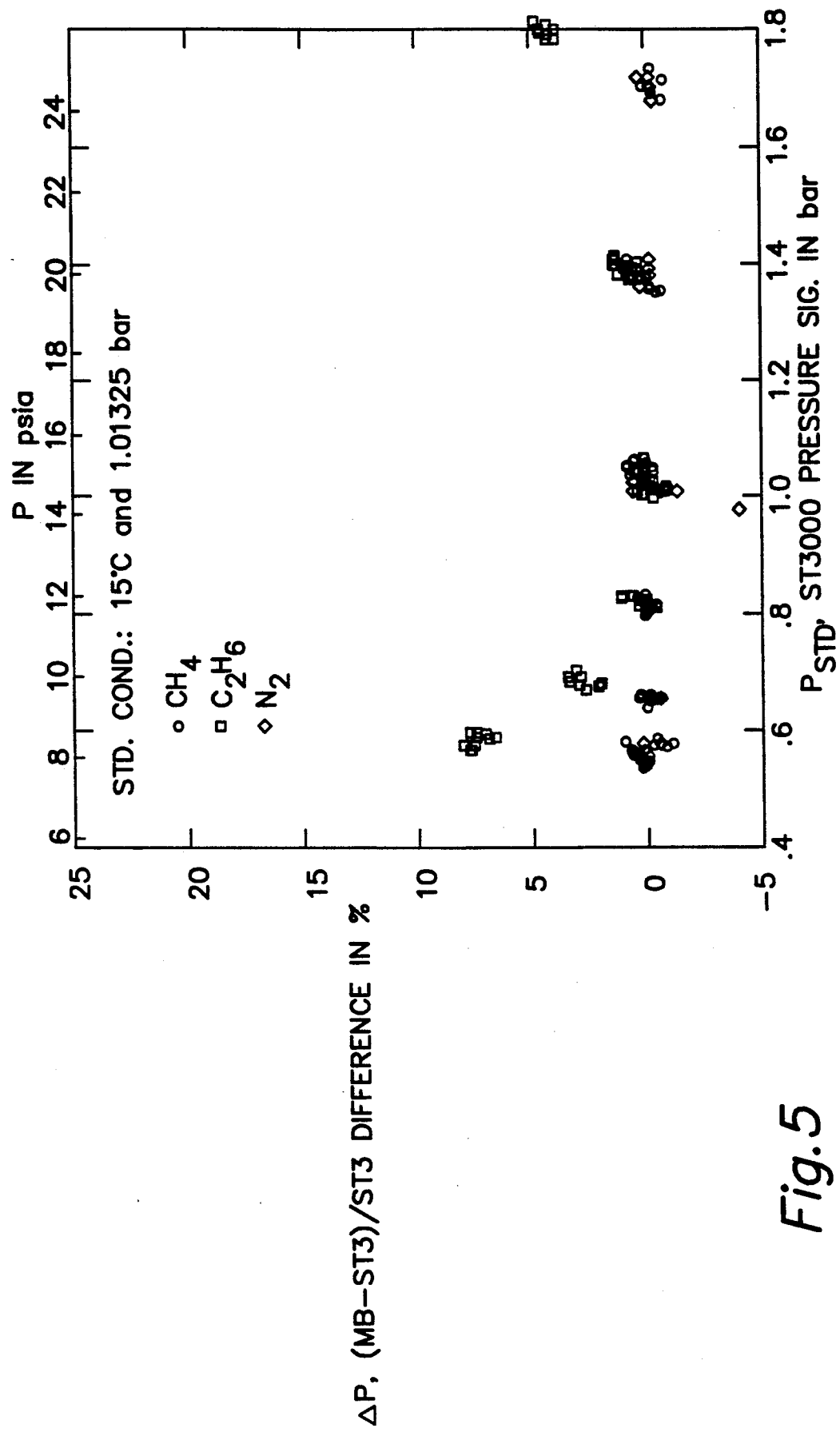
FIG. 5 is a plot of the differences in percent for the comparison of FIG. 4.

FIG. 5 is a plot of the differences in percent that the microbridge system varies from the measurement standard and further illustrates the accuracy of applicant's approach to the determination of absolute pressure.

The embodiments of the invention in which an exclusive property or right is claimed are defined as follows:

1. Apparatus for determining absolute pressure, P, of a gas comprising:

a first microbridge having a first heated element and a thermal sensor thereon, immersed and situated in such proximity to each other and to said gas so as to be thermally coupled by said gas;

$T_g$ measuring sensor for producing a signal, $T_g$, representative of the temperature of said gas;

k and $c_{py}$ computing means for determining thermal conductivity, k, and specific heat, $c_{pv}$, of said gas using said first microbridge;

sensor electronics means for measuring a first current, $H_I$, flowing in said first heated element and producing an electrical signal representative thereof;

sensor electronics means for measuring a first voltage, $H_V$, impressed across said first heated element and providing an electrical signal representative thereof;

a second microbridge having located thereon a second heated element extending over an etched V-groove;

sensor electronics means for measuring a second current, $h_i$ flowing in said second heated element and providing an electrical signal representative thereof;

sensor electronics means for measuring a second voltage, $h_v$ impressed across said second heated element and providing an electrical signal representative thereof;

computing means for determining P based on the electrical signals representative of k, $c_{pv}$, $T_g$ $H_V$, $H_I$, $h_v$, and $h_i$; and output means for providing an output representative of the value of P.

2. The apparatus of claim 1 wherein said means for determining P includes periodically deriving a signal utilizing said k, $c_{pv}$, $T_g$, $H_I$, $H_V$, $h_i$ and $h_v$ as a measure for said absolute pressure P according to a polynomial of the form:

$$P = \Sigma A_i(k^{n1i} c_{pv}^{n2i} T_g^{n3i} H_V^{n4i} H_I^{n5i} h_v^{n6i} h_i^{n7i}) \qquad (3)$$

where
$A_i$ = constants and
n1i, n2i, n3i, n4i, n5i, n6i, and n7i = exponents.

3. The apparatus of claim 2 further comprising:

sensor electronics and microprocessor means for controlling and measuring said $H_V$, $H_I$, $h_v$ and $h_i$ values;

memory means providing said constants and said exponents to said sensor electronics and microprocessor means; and output means providing a signal representative of said absolute pressure P.

4. The process of claim 3 wherein said exponents $n_{1i}$ through $n_{7i}$ in value from $-3$ to $+3$.

5. The apparatus of claim 3 wherein said gas is a fuel gas, air or any other gaseous substance.

6. The apparatus of claim 5 wherein said exponents $n_{1i}$ through $n_{7i}$ range in value from $-3$ to $+3$.

7. Apparatus for determining absolute pressure, P, of a gas when the gas properties of thermal conductivity, k, and specific heat, $c_{pv}$, are determined by using only the signals of a first microbridge having a proximately positioned first heated element and a thermal sensor both immersed and situated in such proximity to each other and said gas so as to be thermally coupled by said gas, further comprising:
  sensor electronics means for measuring a first current, $H_I$, flowing in said first heated element;
  sensor electronics means for measuring a first voltage, $H_V$, impressed across said first heated element;
  a second microbridge having a second heated element extending over an etched V-groove;
  sensor electronics means for measuring a second current, $h_i$ flowing in said second heated element;
  sensor electronics means for measuring a second voltage, $h_v$ impressed across said second heated element; and
  computing means for determining P based on k, $c_{pv}$, $T_g$, $H_V$, $H_I$, $h_v$, and $h_i$ according to a polynomial of the form:

$$P = \Sigma\, A_i (k^{n1i}\, c_{pv}^{n2i}\, T_g^{n3i}\, H_V^{n4i}\, H_I^{n5i}\, h_v^{n6i}\, h_i^{n7i})$$

where
$A_i$ = constants and
n1i, n2i, n3i, n4i, n5i, n6i, and n7i = exponents; and
output means for providing an output representative of the value of P.

8. The apparatus of claim 7 further comprising:
  sensor electronics and microprocessor means for controlling and measuring said $H_V$, $H_I$, $h_v$ and $h_i$ values;
  memory means providing said constants and said exponents to said sensor electronics and microprocessor means; and
  output means providing a signal representative of said absolute pressure P.

9. The apparatus of claim 8 wherein said gas is a fuel gas, air or any other gaseous substance.

10. A process for the measurement of absolute pressure, P, of a gas, comprising the steps of:
  conducting a gas into a chamber having a first microbridge and a second microbridge said microbridges being immersed in said gas;
  measuring the thermal conductivity, k specific heat, $c_{pv}$, and temperature, $T_g$ of said gas at said first microbridge and providing electrical representations thereof;
  measuring the voltage $H_V$ and the current $H_I$ of said first microbridge and providing an electrical representation thereof;
  measuring the voltage $h_v$ and the current $h_i$ of said second microbridge and providing an electrical representation thereof;
  deriving a signal for measurement of absolute pressure, P, of said gas according to a polynomial of the form:

$$\Sigma\, A_i (k^{n1i}\, c_{pv}^{n2i}\, T_g^{n3i}\, H_V^{n4i}\, H_I^{n5i}\, h_v^{n6i}\, h_i^{n7i}) \qquad (5)$$

where
$A_i$ = constants,
n1i, n2i, n3i, n4i, n5i, n6i, and n7i = exponents; and
outputting a representation of the derived value P.

* * * * *